United States Patent
La Thangue et al.

(10) Patent No.: US 9,347,103 B2
(45) Date of Patent: May 24, 2016

(54) SCREENING METHOD

(71) Applicant: Isis Innovation Limited, Oxford (GB)

(72) Inventors: Nicholas B. La Thangue, Bridge of Weir (GB); Susan Fotheringham, North Lanarkshire (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 14/306,137

(22) Filed: Jun. 16, 2014

(65) Prior Publication Data

US 2014/0369999 A1    Dec. 18, 2014

Related U.S. Application Data

(63) Continuation of application No. 12/294,603, filed as application No. PCT/GB2007/001086 on Mar. 27, 2007, now Pat. No. 8,784,806.

(30) Foreign Application Priority Data

Mar. 27, 2006    (GB) .................................. 0606096.6

(51) Int. Cl.
  *C12Q 1/68* (2006.01)
  *C12N 15/11* (2006.01)
  *G01N 33/50* (2006.01)
  *G01N 33/574* (2006.01)

(52) U.S. Cl.
  CPC ............ *C12Q 1/6886* (2013.01); *C12N 15/111* (2013.01); *G01N 33/5011* (2013.01); *G01N 33/574* (2013.01); *G01N 33/57484* (2013.01); *C12N 2310/14* (2013.01); *C12N 2320/10* (2013.01); *C12N 2330/31* (2013.01); *C12Q 2600/106* (2013.01); *C12Q 2600/156* (2013.01); *C12Q 2600/158* (2013.01); *G01N 2333/91045* (2013.01); *G01N 2333/98* (2013.01); *G01N 2500/10* (2013.01); *G01N 2800/52* (2013.01)

(58) Field of Classification Search
  None
  See application file for complete search history.

(56) References Cited

U.S. PATENT DOCUMENTS

| 8,784,806 | B2 | 7/2014 | La Thangue et al. |
| 2005/0118596 | A1 | 6/2005 | Asselbergs et al. |
| 2009/0226894 | A1 | 9/2009 | Grueneberg et al. |

FOREIGN PATENT DOCUMENTS

| EP | 1595952 A1 | 11/2005 |
| WO | 03/035843 A2 | 5/2003 |
| WO | 03/046132 A2 | 6/2003 |
| WO | 03/066885 A2 | 8/2003 |
| WO | 2004/050895 A2 | 6/2004 |
| WO | 2005/023179 A2 | 3/2005 |
| WO | 2005/039498 A2 | 5/2005 |
| WO | 2005/074995 A | 8/2005 |
| WO | 2005/097189 A1 | 10/2005 |
| WO | 2005/100609 A1 | 10/2005 |
| WO | 2006/020016 A2 | 2/2006 |
| WO | 2007/100650 A2 | 9/2007 |

OTHER PUBLICATIONS

Van der Spek et al. (Genomics (31): 20-27, 1996).*
Japanese Patent Application No. 2013-087048, Notification of Reasons for Refusal, mailed Sep. 30, 2014.
U.S. Appl. No. 12/294,603, Restriction Requirement, mailed Sep. 2, 2010.
U.S. Appl. No. 12/294,603, Non-Final Office Action, mailed Apr. 27, 2011.
U.S. Appl. No. 12/294,603, Final Office Action, mailed Dec. 1, 2011.
U.S. Appl. No. 12/294,603, Non-Final Office Action, mailed Mar. 21, 2013.
U.S. Appl. No. 12/294,603, Final Office Action, mailed Nov. 6, 2013.
U.S. Appl. No. 12/294,603, Notice of Allowance, mailed Feb. 3, 2014.
U.S. Appl. No. 12/294,603, Notice of Allowance, mailed Jun. 26, 2014.
Goldie et al. (Cancer and Metastasis Reviews 2011, vol. 20, 63-68).
Cheung et al. (Nature Genetics, 2003, vol. 33, pp. 422-425).
Jackson et al. (Trends in genetics (2004) vol. 20, pp. 521-524).
European Search Report for European Patent Application No. EP 13194854, Apr. 22, 2014, 9 pages.
Office Action for Japanese Patent Application No. JP 2009-502200, Jul. 17, 2013, 3 pages.
Aza-Blanc, P. et al., "Identification of Modulators of TRAIL-Induced Apoptosis Via RNAi-Based Phenotypic Screening," Molecular Cell, Sep. 2003, pp. 627-637, vol. 12.
Echeverri, C.J. et al., "High-Throughput RNAi Screening in Cultured Cells: A User's Guide," Nature Reviews Genetics, May 2006, pp. 373-374, vol. 7.
Japanese Office Action, Japanese Application No. 2009-502200, Oct. 18, 2012, 9 pages.
Mackeigan, J.P. et al., "Sensitized RNAi Screen of Human Kinases and Phosphatases Identifies New Regulators of Apoptosis and Chemoresistance," Nature Cell Biology, Jun. 2005, 15 pages, vol. 7, No. 6.
Moffat, J. et al., "A Lentiviral RNAi Library for Human and Mouse Genes Applied to an Arrayed Viral High-Content Screen," Cell, Elsevier Inc., Mar. 24, 2006, pp. 1283-1298, vol. 124.
Westbrook, T. F. et al., "A Genetic Screen for Candidate Tumor Suppressors Identifies Rest," Cell, Jun. 17, 2005, pp. 837-848, vol. 121.
Zhao, Y. et al., "Inhibitors of Histone Deacetylases Target the Rb-E2F1 Pathway for Apoptosis Induction Through Activation of Proapoptotic Protein Bim," PNAS, Nov. 1, 2005, pp. 16091-16095, vol. 102, No. 44.

(Continued)

*Primary Examiner* — Kimberly Chong
(74) *Attorney, Agent, or Firm* — Kilpatrick Townsend & Stockton LLP

(57) ABSTRACT

This invention relates to a novel screening method that identifies simple molecular markers that are predictive of whether a particular disease condition is responsive to a specific treatment. Also, a method of diagnosing the susceptibility of an individual suffering from a disease to treatment with an HDAC inhibitor is provided. Also provided is a method of treating a proliferative disease or a condition which involves a change in cell differentiation or growth rate in a patient.

17 Claims, 7 Drawing Sheets

(56) References Cited

OTHER PUBLICATIONS

Anderson, La et al., "Regulation of ReIA (p65) Function by the Large Subunit of Replication Factor C," Mol. Cell. Biol., 2003, pp. 721-732, vol. 23, No. 2.
Bedalov, A. et al., "Identification of a Small Molecule Inhibitor of Sir2p," Proc. Natl. Acad. Sci. USA., Dec. 18, 2001, pp. 15113-15118, vol. 98, No. 26.
Brummelkamp, T. R. et al., "Stable Suppression of Tumorigenicity by Virus-Mediated RNA Interference," Cancer Cell, Sep. 2002, pp. 243-247, vol. 2.
Brummelkamp, T. R. et al., "A System for Stable Expression of Short Interfering RNAs in Mammalian Cells," Science, 2002, pp. 550-553, vol. 296.
Butler L.M. et al., "The Histone Deacetylase Inhibitor SAHA Arrests Cancer Cells. Growth, Up-Regulates Thioredoxin-Binding Protein-2 and Down-Regulates Thioredoxin," Proceedings of the National Academy of Sciences of the USA, Sep. 3, 2002, pp. 11700-11705, vol. 99, No. 18.
Della Ragione, F. et al., "Genes Modulated by Histone Acetylation as New Effectors of Butyrate Activity," FEBS Letters, 2001, pp. 199-204, vol. 499, No. 3.
Dyson, N. "The Regulation of E2F by pRb-Family Proteins," Genes Dev., 1998, pp. 2245-2262, vol. 12.
Glaser K.B. et al., "Gene Expression Profiling of Muliple Histone Deacetylase (HDAD Inhibitors: Defining a Common Gene Set Produced by HDAC Inhibition in T24 and MDA Carcinoma Cell Lines," Mol. Cancer Ther., 2003, pp. 151-163, vol. 2.
Glockzin S. et al., "Involvement of the DNA Repair Protein hHR23 in p53 Degradation," Mol. Cell. Biol., 2003, pp. 8960-969, vol. 23, No. 24.
Grozinger, C.M. et al., "Identification of a Class of Small Molecular Inhibitors of the Sirtuin Family of NAD-Dependent Deacetylases by Phenotypic Screening," The Journal of Biological Chemistry, Oct. 19, 2001, pp. 38837-38843, vol. 42.
Inche, A. et al., "Chromatin Control and Cancer Drug Discovery: Realising the Promise," Drug Discovery Today, Feb. 2006, pp. 97-109, vol. 11, No. 3/4.
Jacobson, S. et al., "Modifying Chromatin and Concepts of Cancer," Curr. Op. Genet. Dev. 9, 175-184. 1999.
Johnstone, R. W. "Histone Deacetylase Inhibitors: Novel Drugs for Treatment of Cancer," Nature Reviews Drug Discovery, Apr. 2002, pp. 287-299, vol. 1.
Liang, P. et al., "Analysing Differential Gene Expression in Cancer," Nature Reviews Cancer, Nov. 2003, pp. 869-876, vol. 3.
Marks, P.A. et al., "Histone Deacetylase Inhibitors as New Cancer Drugs," Curr. Opin. Oncol., 2001, pp. 477-483, vol. 6.
McLaughlin, F. et al., "Histone Deacetylase Inhibitors in Psoriasis Therapy," Current Drug Targets, Inflammation and Allergy, 2004, pp. 213-219, vol. 3.
McLaughlin, F. et al., "Tumour Classification for Tailored Cancer Therapy," Annual Reports in Medicinal Chemistry, (Chapter 23), pp. 225-233, vol. 37. 2002.
Mitsiades, C.S. et al., "Transcriptional Signature of Histone Deacetylase Inhibition in Multiple Myeloma: Biological and Clinical Applications," Proc. Natl. Acad. Sci. USA., Jan. 13, 2004, pp. 540-545, vol. 101, No. 2.
Suzuki, H. et al., "A Genomewide Screen for Genes Upregulated by Demethylation and Histone Deacetylase Inhibition in Human Colorectal Cancer," Nature Genetic, Jun. 2002, pp. 141-149, vol. 31, No. 2.
Van Lint, C. et al., "The Expression of a Small Fraction of Cellular Genes is Changed in Response to Histone Hyperacetylation," Gene Expression, 1996, pp. 245-253, vol. 5, No. 4-5.
Vaziri, H. et al., "hSIR2$^{SIRT1}$ Functions as an NAD-Dependent p53 Deacetylase," Cell, Oct. 19, 2001, pp. 149-159, vol. 107.
Archive of "Tissue," Biology-Online.org., Feb. 10, 2006, 1 page, http://www.biology-online.org/dictionary/tissue, [Online] [Archived by http://archive.org on Feb. 10, 2006; Retrieved on Jul. 7, 2011].
Di Gennaro, E. et al., "Acetylation of Proteins as Novel Target for Antitumor Therapy: Review Article," Amino Acids, 2004, pp. 435-441, vol. 26.
Drummond, D.C. et al., "Clinical Development of Histone Deacetylase Inhibitors as Anticancer Agents," Annu. Rev. Pharmacol. Toxicol., 2005, pp. 495-528, vol. 45.
European Partial Search Report, European Application No. 11162743.6, Aug. 9, 2011, 8 pages.
"Homo Sapiens RAD23 Homolog B (S. Cerevisiae) (RAD23B), mRNA," NCBI Database, Database Accession No. NM_002874, May 14, 2011, 6 pages, [Online].
Masutani, C. et al., "Purification and Cloning of a Nucleotide Excision Repair Complex Involving the Xeroderma Pigmentosum Group C Protein and a Human Homologue of Yeast RAD23," The EMBO Journal, 1994, pp. 1831-1843, vol. 13, No. 8.
Shen, M. et al., "Polymorphisms in the DNA Nucleotide Excision Repair Genes and Lung Cancer Risk in Xuan Wei, China," Int. J. Cancer, 2005, pp. 768-773, vol. 116.
Sugasawa, K. et al., "HHR23B, a Human Rad23 Homolog, Stimulates XPC Protein in Nucleotide Excision Repair in Vitro," Molecular and Cellular Biology, Sep. 1996, pp. 4852-4861, vol. 16, No. 9.
Gao, N., et al., "Synergistic antileukemic interactions between 2-medroxyestradiol (2-ME) and histone deacetylase inhibitors involve Akt down-regulation and oxidative stress," Blood, Jan. 1, 2006, pp. 241-249, vol. 107, No. 1.
Jang, E.R., et al., "The histone deacetylase inhibitor trichostatin A sensitizes estrogent receptor α-negative breast cancer cells to tamoxifen," Oncogene, Mar. 4, 2004, pp. 1724-1736, vol. 23.
Keen, C.J., et al., "A novel histone deacetylase inhibitor, scriptaid, enhances expression of functional estrogen receptor α (ER) in ER negative human breast cancer cells in combination with 5-aza 2"-deoxycytidine," Breast Cancer Research and Treatment, 2003, pp. 177-189, vol. 81.
Nimmanapalli, R., et al., "Cotreatment with the histone deacetylase inhibitor suberoylanilide hydroxamic acid (SAHA) enchances imatinib-induces apoptosis of Bcr-Abl-positive human acute leukemia cells," Blood, Apr. 15, 2003, pp. 3236-3239, vol. 101, No. 8.
Yu, C., et al., "Histone Deacetylase inhibitors promote STI571-mediated apoptosis in STI571-sensitive and—resistant Bcr/ABL+ human myeloid leukemia cells[1]," Cancer Research, American Association for Cancer Research, May 1, 2003, pp. 2118-2126, vol. 63.
Zhu, W-G., et al., "The Interaction of Histone Deacetylase Inhibitors and DNA Methyltransferase Inhibitors in the Treatment of Human Cancer Cells," Current Medicinal Chemistry, Anti-Cance Agents, 2003, pp. 187-199, vol. 3.
PCT International Search Report and Written Opinion, PCT/GB2007/001086, Oct. 17, 2007.
Minucci, S. and P. Pelicci, "Histone deacetylase inhibitors and the promise of epigenetic (and more) treatments for cancer," Nature, vol. 6, pp. 38-51 (Jan. 2006).

* cited by examiner

FIG. 1(b)

| Pool number | Colony harvest | | | |
|---|---|---|---|---|
| | 1 | 2 | 3 | 4 |
| 11 | | | | |
| 14 | | | | |
| 28 | 1 | 1 | 1 | 1 |
| 29 | | | | |
| 33 | | | | |
| 37 | 3 | 1 | | |
| 46 | 1 | | 3 | |
| 51 | 20 | 4 | 5 | 21 |
| 52 | 19 | 31 | | 16 |
| 53 | 1 | | | |
| 70 | 4 | | | |
| 72 | | | | |
| 74 | 2 | | | |
| 77 | | | | |
| 81 | | | | |
| TOTAL COLONIES | 51 | 37 | 6 | 38 |

FIG. 2(a)

| Probability | Gene | Gene ID | Name | Pool | Colony | No. hits | Pool ID Match | Sequence |
|---|---|---|---|---|---|---|---|---|
| high | hHRAD23B | NM_002874 | human rad 23B | 52 | 1 | 2 | yes | GATGCAACGAGTGCACTTG |
| | RFC1 | NM_002913 | replication factor C1 | 52 | 3 | 2 | yes | CAGATTAAGGGTGCTATGA |
| | MYD88 | NM_002468 | myeloid differentiation primary response gene 88 | 52 | 4 | 1 | yes | ACACAACTTCAGTGCGATAG |
| | PTBP1 | NM_002819 | polypyrimidine tract binding protein 1 | 52 | 8 | 1 | yes | GGACCGTTTATCATGAGC |
| | PPP4R1 | NM_005134 | protein phosphatase 4 regulatory subunit 1 | 46 | 1 | 1 | yes | ACACAGCTTTCCACAGGGC |
| | LIF | NM_002309 | leukaemia inhibitory factor | 51 | 4 | 1 | yes | CAACCTGGACAAGCTATGT |
| | LIFR | NM_002310 | leukaemia inhibitory factor receptor | 51 | 9 | 1 | yes | CAGGCCGTGGTACTACCACGGCCTG |
| | | | | 51 | 3 | 1 | yes | TAATCAGTACTACCACGGCCTG |
| medium | SCGB2A2 | NM_002411 | secretoglobin, family 2A, member 2 | 51 | 19 | 1 | yes | TTAATATATGACAGCAGTC |
| | | | | 51 | 20 | 1 | yes | TTAATATATGACAGCAGTC |
| low | HLA-DQB1 | NM_002123 | major histocompatibility complex, class II, DQ beta 1 | 51 | 11 | 1 | yes | GAGATCGTGCGCTTCGACA |
| | PVRL1 | NM_002855 | poliovirus receptor-like 1 | 52 | 9 | 1 | yes | GTGCAGTATNAGCCTGAG |
| | SERPA10 | NM_016186 | serpin A10 | 74 | 2 | 2 | yes | AGATCTCCATGAGGCACGA |
| | HEXB | NM_000521 | hexosaminidase B | 70 | 1 | 1 | yes | ACATGAGACAAAGATAGC |
| | PPAT | NM_002703 | phophoribosylpyrophosphate amidotransferase | 52 | 5 | 1 | yes | ATCACGTCTTTACTGAAGA |
| | LDHB | NM_002300 | lactate dehydrogenase B | 51 | 15 | 2 | yes | GGATATACCAACTGGGCTA |
| | MAN2A1 | NM_002372 | mannosidase 2A member 1 | 51 | 2 | 3 | yes | GTTAAGCCGCCAGTTCACC |
| | | | | 51 | 14 | 1 | yes | GTTAAGCCGCCAGTTCACC |
| | PLECK2 | NM_016445 | pleckstrin 2 | 74 | 1 | 2 | yes | GAAATTAGCCTGAGCACTG |
| | | | | 28 | 1 | 2 | no (74) | GAAATTAGCCTGAGCACTG |
| | | | | 37 | 2 | 1 | no (74) | GAAATTAGCCTGAGCACTG |
| | SART2 | NM_013352 | squamous cell carcinoma antigen recognised by T cell | 51 | 7 | 1 | no (56) | TTAACNGGACAAACTATGT |

FIG. 2(b)

| Gene | Name(s) | | Main function | Localisation | Associated proteins |
|---|---|---|---|---|---|
| RFC-1 | replication factor C1 | | facilitates loading of PCNA at sites of DNA synthesis | nucleus | BRCA1, ATM, Rb, C/EBPa, HDAC1 |
| hHR23B | human Rad23B | p140 | modulates the transfer of proteins from site of ubiquitination to the proteasome | nucleus/cytoplasm | 19S proteasome component, hdm2, p53 |
| PP4R1 | protein phosphatase 4 regulatory subunit 1 | | binds to and regulates phosphatase activity of PP4 catalytic subunit | nucleus/cytoplasm | PP4C, HDAC3 |
| MYD88 | myeloid differentiation marker 88 | | general adaptor molecule involved in Toll-receptor family signalling | nucleus/cytoplasm | NF-κB, IL1RAP, IRAK2 |
| PTBP1 | polypyrimidine tract binding protein 1 | hnRNP I | RNA chaperone involved in pre-mRNA splicing | nucleus/cytoplasm | Apaf-1, TLS/FUS |
| LIF | leukaemia inhibitory factor | | polyfunctional cytokine | cytoplasm | HGF, BMP2 |
| LIFR | leukaemia inhibitory factor receptor a-subunit | LIFRα | complexes with gp130 to form the LIF receptor, involved in signalling of a variety of cytokines | cell membrane | LIF, SHP-2 |

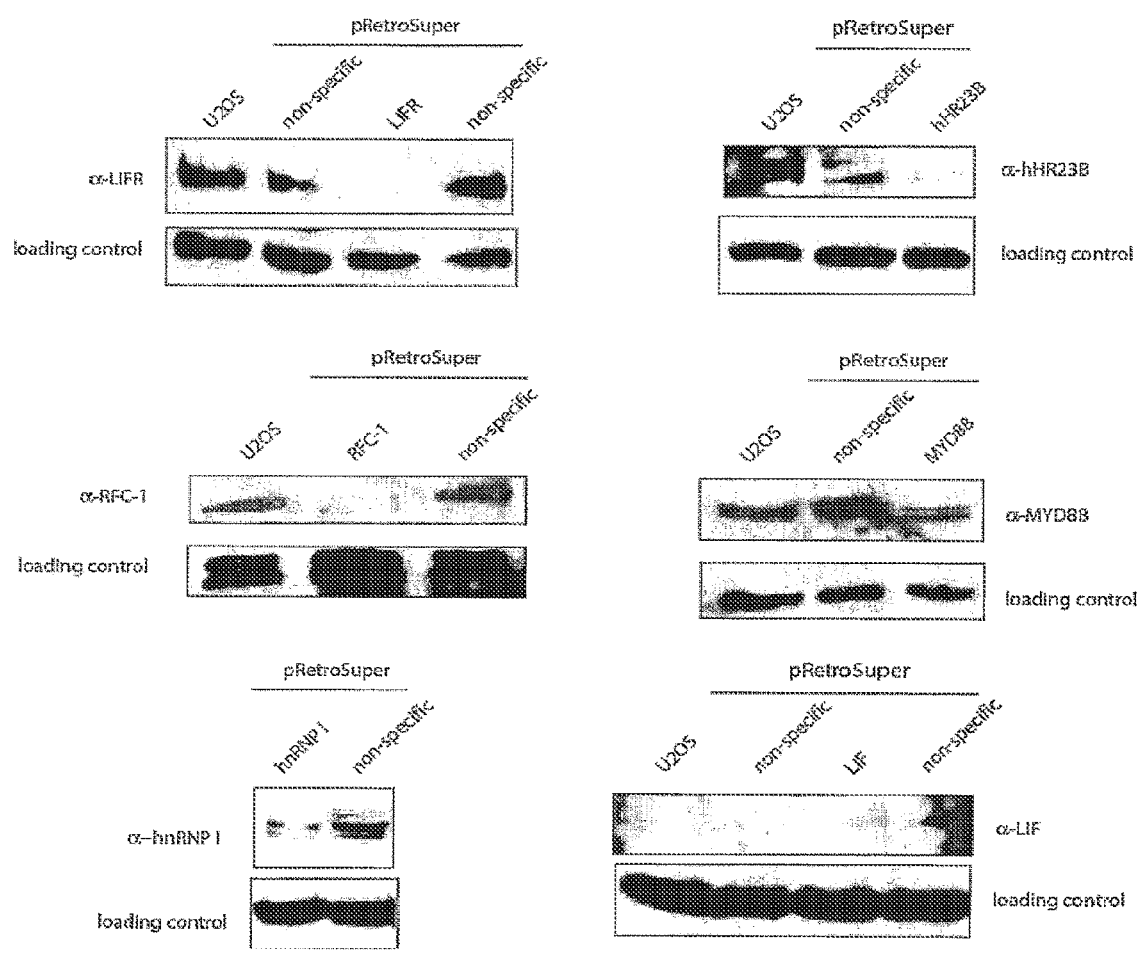

SCREENING METHOD

CROSS-REFERENCE TO RELATED APPLICATIONS

This application is a continuation of U.S. application Ser. No. 12/294,603, filed Mar. 27, 2007, which is the National Stage of International Application No. PCT/GB2007/001086, published in English under PCT Article 21(2), filed Mar. 27, 2007, which claims priority to United Kingdom Patent Application No. 0606096.6, filed on Mar. 27, 2006, the entire contents of which are hereby incorporated by reference.

SEQUENCE LISTING

This application contains a Sequence Listing which has been submitted in Computer Readable Form (CRF) via EFS-Web and is hereby incorporated by reference in its entirety. Said CRF copy, created on Mar. 24, 2015, is named SUBSEQTXT_921379.txt and is 8,996 bytes in size.

The invention relates to a novel screening method that identifies simple molecular markers that are predictive of whether a particular disease condition is responsive to a specific treatment. The method thus streamlines programs for drug development, and informs on how a drug can be used in a clinical setting.

A significant proportion of therapeutic drug candidates fail to become marketable drugs because of adverse metabolism or toxicity discovered during clinical trials. Furthermore, many drugs that enter the clinical setting exhibit limiting efficacy and toxicity. These failures represent a very significant waste of development expenditure and consequently there is a need for new technologies that can more reliably, quickly and economically predict at the pre-clinical development stage the metabolic and toxicological characteristics of drug candidates and their likely efficacy in the prevention or treatment of disease.

The development of new therapies is complicated and expensive. Taking the example of cancer, this is a complex genetic disease for which successful therapies have proven elusive. Furthermore, in the clinical context, tumours frequently acquire resistance to new treatments. There is thus a great need to develop simple tests that predict tumour sensitivity to new and existing drugs. The same applies to other disease conditions, particularly those in which cell proliferation contributes to the disease pathology.

SUMMARY OF THE INVENTION

According to the invention, there is provided a method for identifying a biomarker that correlates with the sensitivity of a disease to a drug, the method comprising:
 a) exposing a cell to:
 i) the drug;
 ii) a compound which inhibits the level or activity of a protein in the cell;
 b) monitoring for a phenotype in the cell;
 wherein the occurrence of a phenotype in the cell that differs from the phenotype evident when the cell is treated with drug alone identifies the protein or its encoding gene as a biomarker that correlates with drug sensitivity.

The invention is a screen that allows disease biomarkers to be identified. The type of biomarker which can be identified predicts disease sensitivity to new or existing drugs, and thus allows patients to be stratified into likely responder and non-responder groups. These biomarkers will improve the probability of clinical success during drug development, and maximise the therapeutic benefit to the patient by "tailoring" the therapy to the disease.

The invention is particularly applicable to proliferative conditions such as cancer and diseases which involve a change in cell differentiation or growth rate. However, any disease that expresses a biomarker identified according to the invention is a candidate for treatment with the tested drug.

The technology of the invention is ideally suited to drugs where the route to achieve maximum clinical efficacy is unclear. Equally, the screen delivers information on critical genes that are required for drug action. For example, for cancer drugs, the screen identifies the crucial pathways that are involved in killing tumour cells.

In the approach of the invention, the method involves exposing a cell or population of cells to two entities. The cells are exposed to a drug, since it is this entity that is under investigation; this makes the method specific for that particular drug. Second, the cells are exposed to a compound that modulates the level or activity of a protein that is potentially required for susceptibility to the drug. As a result of the design of this methodology, if a differential phenotype is manifested as a result of the exposure of the cells to the drug as compared to cells that have been exposed to drug but which have not been exposed to the inhibitory compound, then this indicates that the protein whose level or activity has been modulated may be implicated in the mechanism of action of the drug and thus identifies this protein as a useful biomarker.

The working of the methodology can be exemplified with an example in which a genome-wide siRNA knock-down screen is used to identify functionally-important genes that influence sensitivity to Histone deacetylase (HDAC) inhibitors. HDAC inhibitors are a particularly relevant group of new cancer agents. Chemically-distinct HDAC inhibitors are in clinical development, in particular including peripheral T-cell lymphoma, cutaneous T-cell lymphoma, chronic lymphocytic leukaemia and androgen-independent prostate cancer. However, the clinical utility (for example responsive tumour, stage of disease, relevant drug combination) is, at the current time, impossible to predict. Biomarkers that inform on tumour sensitivity patterns would provide a very important step forward, both in maximising the clinical benefit of the drug and differentiating between HDAC inhibitors. The example described, whilst focussed on HDAC inhibitors, has equal application to other classes of mechanism-based therapies in which a slow-down of cell growth, differentiation or proliferation is required for the disease to be successfully treated.

Herein, the screening platform has been validated with studies on HDAC inhibitors, utilising an siRNA library that targets human genes that have been selected on the association with cancer and other human diseases. HDAC inhibitors kill tumour cells. Tumour cells treated with the siRNA library and an appropriate HDAC inhibitor survive due to the loss of a gene that is targeted by the siRNA. They survive by avoiding apoptosis that would otherwise have been induced by the HDAC inhibitor had the gene been present and active within the cell. That is, the gene needs to be expressed in order to confer sensitivity to the HDAC inhibitor. Accordingly, this methodology identifies as biomarkers, genes that are targets for HDAC inhibitors. FIG. 1 depicts an illustration of how the methodology works.

The method of the invention assesses the response of a cell to a particular drug by identifying disease biomarkers. The invention can thus be used in many different ways to evaluate the suitability of a particular cell to treatment with a particular drug.

One example is in the clinic during diagnosis, for example, of tumour cells taken from a particular patient. If these hypothetical tumour cells are found to have high levels of gene X or active protein encoded by gene X, and gene X is identified by the methodology of the invention as being implicated in susceptibility to a particular drug or drug combination, then that drug or combination of drugs is a good candidate for therapy in that patient and the tumour is likely to respond better to the drug. Conversely, if gene X or its encoded protein is only present at low levels then the tumour is unlikely to respond well to that particular drug.

Quantitative effects of drugs or drug combinations can also be measured. For example, the compound which inhibits the level or activity of the protein in the cell may be used in separate tests to inhibit a gene by different degrees and cell phenotype can be monitored in these separate tests, optionally also under different drug conditions. By different drug conditions is meant to include different drug concentrations, different times of drug exposure, different drug combinations and so on. Of course, various combinations of different drug concentrations, exposure times and combinations can also be tested in this system.

In the clinical setting, it will also be very interesting to explore the temporal regulation of biomarkers during disease progression since the efficacy of drugs and drug combinations vary through the various stages of disease progression. At present, there are very limited methods by which such variation can be assessed. The invention allows temporal effects to be assessed with a view to devising treatments that are not only bespoke to each patient but also to the particular stage of the disease.

The invention also allows assessment of the degree to which particular diseases such as tumours are susceptible to mutation. Expression in normal tissue and any polymorphic influence within the patient population will also be amenable to study using this tool.

It is also possible to deconvolute the mechanism of drug treatment. For example, it is possible to assess how drug treatment impacts on expression level.

Another application allows drug companies to position their drugs and lead compounds more effectively. Drugs that show promise during their development for the treatment of a particular disease generally do so because of a perceived mechanism of action that may only be partially understood. The method of the invention allows dissection of a mechanism of action of a drug so that its full potential can more easily be realised. This is possible because of the facility to demonstrate differences in efficacy between different patient subgroups (e.g. on the grounds of gender or race), different disease stages, different gene polymorphisms (e.g. P450, or Fc Receptor) and so on.

It is often the case that a number of drug companies have compounds in clinical development for the same target. The invention allows a company to position its drug relative to others, either for a particular disease, or a stage of disease, or a patient group. This will assist a company in differentiating its own drug's efficacy, in proving value to drug approval agencies that are currently on heightened safety alert and in pushing new treatment paradigms at a time of high skepticism of drug companies' motives, and rising cost-sensitivity among payers.

A related application of the invention will be in finding new, safe and effective applications for drugs that have exhibited adverse side-effects or proven ineffective in treating the conditions for which they were originally prescribed.

An example is provided by the class of CDK inhibitors, which show promising anti-tumour efficacy in vitro but which have not to date been shown to be effective in vivo. This is probably because researchers have not yet explored their mechanism of action precisely enough to tailor their use for a clinical setting. The method of the invention will allow this precise mechanism of action to be investigated.

There are also numerous examples of drugs that have been withdrawn from the market. An example is Merck's voluntary worldwide withdrawal of Vioxx (rofecoxib), a COX-2 selective non-steroidal anti-inflammatory drug (NSAID) used to relieve signs and symptoms of arthritis, acute pain, and painful menstrual cycles, because of evidence that the drug may cause an increased risk in cardiovascular events such as heart attack and strokes during chronic use. It is very likely that safe and effective therapies do exist for Vioxx, but there are very limited existing methods by which such therapies might be identified. In contrast, the invention allows such an approach.

Another application for the screen of the invention will be in identifying tissues or even patients that are likely to suffer toxic effects from administration of a drug. For example, if a particular gene, identified as necessary for susceptibility to a drug, is expressed at a high level in a normal, non-diseased tissue, this tissue can be identified as sensitive to the drug. This information can be used to limit the toxicity in healthy tissues. This is commonly seen with many drugs, particularly anti-cancer drugs.

Biomarkers that predict disease sensitivity, whilst important in the clinical setting, could have important implications too for understanding the mechanism of action of new drugs. Again using the cancer field as an example, HDAC inhibitors are known to be profound apoptotic agents. Mechanistically, however, the identity of crucial downstream targets that mediate the apoptotic outcome is not clear. The biomarkers identified using the method of the invention will provide important mechanistic clues in explaining how tumour cells enter apoptosis.

The method of the invention involves exposing the cell to i) the candidate drug; ii) a compound that modulates the level or activity of a protein that is potentially required for susceptibility to the drug.

The candidate drug may be any drug. Examples include drugs proposed for treatment of cell proliferative disorders, autoimmune/inflammatory disorders, cardiovascular disorders, neurological and psychiatric disorders, developmental disorders, genetic disorders, metabolic disorders, infections and other pathological conditions. Of particular relevance are diseases in which aberrant cell proliferation plays a role, and including cancer, neoplasm, brain tumour, glioma, bone tumour, lung tumour, breast tumour, prostate tumour, colon tumour, haemangioma, myeloproliferative disorder, leukaemia, haematological disease, angiogenesis disorders, dermatological disease, fibrosis, cardiovascular disease and endometriosis. Similar examples will be known to those of skill in the art.

One example of a preferred class of drugs, for which the invention has been exemplified herein, is the class of HDAC inhibitors. Other examples will be apparent to those of skill in the art, and include aurora kinase inhibitors, cdk inhibitors, mTOR inhibitors and natural products such as quercetin and analogues thereof, particularly natural products for which there may be multiple targets and pathways.

A combination of drugs may also be tested according to the invention. For example, certain drugs are known to work well in combination, either through additive or synergistic effects. Equally, many drugs do not work well in combination either because their mechanistic effects are not compatible or because they interact together. All these scenarios may be evaluated according to the invention by testing combinations of drugs together. Combinations may include two, three, four, five, six or more distinct drugs. When applied in combination, drugs may be used at the same concentration or different concentrations. Drugs may be used at their recommended dosage or within a recommended dosage range. Alternatively, drugs can be used at lower or higher concentration than their recommended dosage, for example, to explore potentially unexplored mechanisms or to investigate the potential for side-effects of overdosing.

According to the invention, a cell is exposed to the drug. Generally, a population of cells will be exposed to the drug. By "exposed" is meant that the cell is contacted with the drug so that its effects may be manifested. Generally, the most appropriate form of exposure involves incorporation of the drug within the medium in which the cell is growing, at a suitable concentration. The drug may of course be applied to different populations of cells in different concentrations and by doing so a dose response evaluation may be performed.

The cell is also exposed to a compound that modulates the level or activity of a protein that is potentially required for susceptibility to the drug. One advantage of the invention is that the mechanism of action of a drug can be explored without any existing knowledge of its mechanism of action, or preconception of how it is working. Accordingly, one appropriate method for performing the invention involves exposure of a population of cells to a library of compounds, in which each compound in the library targets a gene or protein that is potentially implicated in the mechanism of action of the drug.

The compound must modulate the level or activity of a protein which is potentially implicated in the mechanism of action of a particular drug. The term "modulate" includes reduction as well as enhancement. The activity or level of the protein may be modulated by 10%, 20%, 40%, 80%, 150%, 500%, 1000% or more of its wild type intensity. Preferably, the compound may reduce, inhibit or "knock-out" the expression level or activity of the protein. More preferably, the compound may reduce, inhibit, or knock-out the expression level of the protein. The compound preferably reduces the expression level to within less than 50%, 25%, 10%, 1%, 0.1%, 0.01%, 0.001% or less of its wild type level.

Examples of nucleic acid compounds that may be used according to the invention include RNAi, shRNA, siRNA, ribozymes and antisense nucleic acid, such as antisense RNA. In theory, libraries of antibodies or small molecule compounds could be used. Particularly preferred is the use of RNAi and, specifically, shRNA that in due course generates siRNA molecules. siRNA may be delivered using vectors, particularly viral vectors, or may be introduced directly into cells as synthetic siRNA. One problem with using direct introduction of synthetic siRNA is the short half-life, which makes long term effects on gene expression poor. However, advances in siRNA technology are likely to improve half life significantly over the coming years.

For example, cells may be exposed to a library of siRNA vectors that incorporate within the cells. The multiplicity of infection can be organised such that on average each cell incorporates a single vector and this vector expresses an siRNA species that knocks-down expression of a particular gene. Accordingly, in each cell, the expression of one gene is knocked out, so allowing the effects of the drug to be evaluated in the absence of that gene. If the cell survives despite the presence of drug, it can be inferred that the gene is required for drug sensitivity. Accordingly, cells in which that particular gene is overexpressed represent good candidates for effective treatment with that drug.

Preferably, according to the invention, a vectored RNA interference library is used. This may be a viral vectored RNA interference library, for example, using lentivirus, adenovirus (Galapagos, Belgium), pox viruses and so on (see, for example, Chen et al., 2005, J. RNAi and Gene Silencing, 1(1); 5-11). Viral based libraries (including retroviral libraries) work well because these result in efficient delivery of nucleic acid into cells. Expression levels can be lower, for example, because retroviruses integrate into DNA and are thereby influenced by the chromatin environment, although again it is anticipated that improvements over the coming years will reduce this problem.

Variations on the idea of using libraries are of course possible, as the skilled person will appreciate. For example, in the case of siRNA libraries, the multiplicity of infection may be varied, for example, between less than 1 and more than 100 to ensure that gene knock-down occurs efficiently. Furthermore, different compounds (e.g. siRNAs) can be used, targeting different parts of a selection of genes (e.g. 10, 100, 1000, 10000), or even different parts of a single gene. For instance, compounds (e.g. siRNAs) against different parts of a single gene could be used to explore the differential effects of splice variants.

It would also be possible to make the effect of the inhibitory compounds conditional, for example, using inducible promoters such that expression of a compound (e.g. siRNAs) is made conditional on the presence of a particular inducing agent that can be administered when required.

A library of compounds used as described above preferably targets a number of different genes, for example, greater than 100, greater than 1000, greater than 10,000, greater than 15,000, greater than 20,000, greater than 25,000, greater than 30,000, greater than 35,000, or more. The genes targeted by the compounds of the library may be genome-wide (examples are made by Qiagen, Hilden, Germany; also Dharmacon, Lafayette, USA). Large-scale libraries have also recently been constructed by academic researchers (Paddison et al., 2004, Nature 428; 427-431; Berns et al., 2004, Nature, 428; 431-437; Michiels et al., 2002, Nat. Biotechnol. 201154-1157) and commercially (Galapagos, Belgium; Genordia AB, Sweden). The genes targeted by the compounds of the library may be specific to a particular disease (e.g. cancer, neurogenerative disease, inflammatory disorders).

The screen that has been exemplified herein utilises an siRNA library that targets approximately 13,000 human genes that have been selected on the association with cancer and other human diseases. Cells treated with the siRNA library and an appropriate drug survive due to the loss of a gene that is targeted by the siRNA. They survive by avoiding apoptosis that would otherwise have been induced by the HDAC inhibitor had the gene been present and active within the cell.

The results of the methodology are assessed by looking for a phenotype in the cell. Preferably, the phenotype in the cell is measured by comparison to control cells. Suitably, control cells have been treated with the candidate drug but have not been exposed to the compound that modulates the level or activity of the protein that is potentially required for susceptibility to the drug. In this way, any phenotype that is observed can be tied specifically to the effects of the compound.

Any phenotypic difference between treated cells and control cells is potentially of interest. A phenotype may relate to the general function or appearance of the cell, or may be a molecular phenotype, such as an increase or decrease in the level or activity of a particular protein. In this sense, a specific phenotype may be tested for, using molecular techniques such as RT-PCR, immunohistochemistry, Western blotting, DNA blotting and so on.

In one preferred embodiment, the observed phenotype may be the survival or growth characteristics of the cell. For example, in the illustration of the invention that is described above using siRNA vectors to knock out expression of a particular gene, survival is indicative of knock-out of a gene that is required for susceptibility to the drug. Survival can be measured in a number of different ways, as the skilled person will understand. Examples include cell viability and survival assays which are well known in the art. In the examples used herein, cell survival was monitored by looking for the appearance of colonies on plates co-treated with drug and the siRNA-encoding viral library.

According to a further aspect of the invention various genes have been implicated in the susceptibility of cells to HDAC inhibitors. These discoveries allow a number of developments. For example, tumours can be stratified into groupings that are likely to undergo more favourable responses to HDAC inhibitors. Specific evaluations can be made of a patient's expression profile for one or more of these genes, and based on these evaluations, a diagnosis can be formulated as to whether the patient is a suitable candidate for treatment with an HDAC inhibitor. If so, a more detailed evaluation can then be made as to what form the treatment should best take (e.g. dosage, time and method of administration, drug combination).

It is also likely that screens of the type described herein will identify known therapeutic targets such as enzymes as determinants of drug sensitivity. Information such as this will therefore predict likely combinations of drugs that will be effective in the clinic. For example, in the context of HDAC inhibitors, it may be that such inhibitors can be used to treat tumours in conjunction with a drug against a therapeutic target identified in the screen.

These discoveries also progress our mechanistic understanding of the method of action of HDAC inhibitors. Herein, we have identified the critical regulatory pathways affected by HDAC inhibitors and necessary for the apoptotic outcome. We hypothesise that the proteins identified through the knock-down screen may themselves be modified by acetylation, or alternatively may interact with other proteins subject to acetylation control, allowing them to be modified and function in pathways required for apoptosis. Elucidating the role of these novel effector proteins will identify essential pathways which are targeted by HDAC inhibitors and necessary for the induction of apoptosis.

For example, these discoveries allow the development of regulators, such as small drug molecules, that affect the activity of the proteins encoded by these genes, so allowing diseases and physiological conditions that are treatable using HDAC inhibitors to be refined. For example, such regulator molecules may affect the acetylation state of these proteins, or may affect their ability to interact with other proteins that are subject to acetylation by HDAC inhibitors.

Genes identified herein with high confidence as being essential for susceptibility to the action of HDAC inhibitors include those listed in FIG. 2 herein. These genes are hHRAD23B (NM_002874; human rad 23B); RFC1 (NM_002913; replication factor C1); MYD88 (NM_002468; myeloid differentiation primary response gene 88); PTBP1 (NM_002819; polypyrimidine tract binding protein 1); PPP4R1 (NM_005314; protein phosphatase 4 regulatory subunit 1); LIF (NM_002309; leukaemia inhibitory factor); LIFR (NM_002310; leukaemia inhibitory factor receptor). Other genes identified include SCBGB2A2 (NM_002411; secretoglobin, family 2A, member 2); HLA-DQB1 (NM_002123; major histocompatibility complex, class II, DQ beta 1); PVRL1 (NM_002855; poliovirus receptor-like 1); SERPA10 (NM_016186; serpin A10); HEXB (NM_000521; hexosaminidase B); PPAT (NM_002703; phophoribosylpyrophosphate amidotransferase); LDHB (NM_002300; lactate dehydrogenase B); MAN2A1 (NM_002372; mannosidase 2A member 1); PLECK2 (NM_016445; pleckstrin 2); and SART2 (NM_013352; squamous cell carcinoma antigen recognised by T cell).

These discoveries allow the development of diagnostic agents and methods that are suitable for assessing a particular patient or patient sample for susceptibility to treatment with an HDAC inhibitor, such that tumours can be stratified into groupings that are likely to undergo more favourable responses to HDAC inhibitors. It also paves the way for the identification of mutations and polymorphisms (such as SNPs) within genes coding for these proteins, so allowing the assessment of an individual patient's potential for treatment using an HDAC inhibitor.

This aspect of the invention provides a method of diagnosing the susceptibility of an individual suffering from a disease to treatment with an HDAC inhibitor, the method comprising assessing the sequence, or level of expression or activity of any one of the genes from the group of hHRAD23B, RFC1, MYD88, PTBP1, PPP4R1, LIF, LIFR, SCBGB2A2, HLA-DQB1, PVRL1, SERPA10, HEXB, PPAT, LDHB, MAN2A1, PLECK2 and SART2, or their expression products, in tissue from said patient and comparing said sequence, level of expression or activity to a reference, wherein a sequence, level of expression or activity that is different to said reference is indicative of an altered susceptibility to treatment with the HDAC inhibitor relative to the reference state. Generally, a level that is significantly higher than the reference level will indicate that the individual is more susceptible to treatment with the HDAC inhibitor. A level that is significantly lower than the reference level is indicative of an individual's potential resistance to treatment with the HDAC inhibitor. By "significant" is meant that the level of expression or activity is more than 10%, 25%, 50%, 100%, 250%, 500%, 1000% or more, lower than the reference level.

The expression product is preferably a protein, although alternatively mRNA expression products may be detected. If a protein is used, the protein may be detected by an antibody which preferably binds specifically to that protein. The term "binds specifically" means that the antibodies have substantially greater affinity for their target polypeptide than their affinity for other related polypeptides, and preferably do not cross-react with other proteins. As used herein, the term "antibody" refers to intact molecules as well as to fragments thereof, such as Fab, F(ab')2 and Fv, which are capable of binding to the antigenic determinant in question. By "substantially greater affinity" we mean that there is a measurable increase in the affinity for the target polypeptide of the invention as compared with the affinity for other related polypeptide. Preferably, the affinity is at least 1.5-fold, 2-fold, 5-fold 10-fold, 100-fold, $10^3$-fold, $10^4$-fold, $10^5$-fold, $10^6$-fold or greater for the target polypeptide. Preferably, the antibodies bind to the detected protein with high affinity, preferably with a dissociation constant of $10^{-4}$M or less, preferably $10^{-7}$M or less, most preferably $10^{-9}$M or less; subnanomolar affinity (0.9, 0.8, 0.7, 0.6, 0.5, 0.4, 0.3, 0.2, 0.1 nM or even less) is preferred.

For example, the method may comprise the steps of: (a) contacting a ligand of hHRAD23B, RFC1, MYD88, PTBP1, PPP4R1, LIF, LIFR, SCBGB2A2, HLA-DQB1, PVRL1, SERPA10, HEXB, PPAT, LDHB, MAN2A1, PLECK2 or SART2, such as an antibody against one of these proteins, with a biological sample under conditions suitable for the formation of a ligand-protein complex; and (b) detecting said complex.

Where mRNA expression product is used, it is preferably detected by the steps of contacting a tissue sample with a probe under stringent conditions that allow the formation of a hybrid complex between the mRNA and the probe; and detecting the formation of a complex. Preferred methods include comparing the amount of complex formed with that formed when a control tissue is used, wherein a difference in the amount of complex formed between the control and the sample indicates the presence of cancer. Preferably the difference between the amount of complex formed by the test tissue compared to the normal tissue is an increase or decrease. More preferably a two-fold difference in the amount of complex formed is deemed significant. Even more preferably, a 3-fold, 4-fold, 5-fold, 10-fold, 20-fold, 50-fold or even 100-fold increase or decrease in the amount of complex formed is significant.

In this alternative methodology, the method may comprise the steps of: a) contacting a sample of tissue from the patient with a nucleic acid probe under stringent conditions that allow the formation of a hybrid complex between a nucleic acid molecule coding for hHRAD23B, RFC1, MYD88, PTBP1, PPP4R1, LIF, LIFR, SCBGB2A2, HLA-DQB1, PVRL1, SERPA10, HEXB, PPAT, LDHB, MAN2A1, PLECK2 or SART2 and the probe; b) contacting a reference sample with the probe under the same conditions used in step a); and c) detecting the presence of hybrid complexes in said samples; wherein detection of levels of the hybrid complex in the patient sample that differ from levels of the hybrid complex in the reference sample is indicative of an altered susceptibility to treatment with the HDAC inhibitor relative to the reference state of disease.

The method may comprise the steps of: a) contacting a sample of nucleic acid from tissue of the patient with a nucleic acid primer under stringent conditions that allow the formation of a hybrid complex between a nucleic acid molecule encoding hHRAD23B, RFC1, MYD88, PTBP1, PPP4R1, LIF, LIFR, SCBGB2A2, HLA-DQB1, PVRL1, SERPA10, HEXB, PPAT, LDHB, MAN2A1, PLECK2 or SART2 and the primer; b) contacting a reference sample with the primer under the same conditions used in step a); c) amplifying the sampled nucleic acid; and d) detecting the level of amplified nucleic acid from both patient and reference samples; wherein detection of levels of the amplified nucleic acid in the patient sample that differ significantly from levels of the amplified nucleic acid in the reference sample is indicative of an altered susceptibility to treatment with the HDAC inhibitor relative to the reference state.

The method may comprise the steps of: a) obtaining a tissue sample from a patient being tested for disease; b) isolating a nucleic acid molecule encoding hHRAD23B, RFC1, MYD88, PTBP1, PPP4R1, LIF, LIFR, SCBGB2A2, HLA-DQB1, PVRL1, SERPA10, HEXB, PPAT, LDHB, MAN2A1, PLECK2 or SART2 from the tissue sample; and c) diagnosing the patient by detecting the presence of a mutation which is associated with an altered susceptibility to treatment with the HDAC inhibitor. This method may further comprise amplifying the nucleic acid molecule to form an amplified product and detecting the presence or absence of a mutation in the amplified product. The presence or absence of the mutation in the patient may be detected by contacting the nucleic acid molecule with a nucleic acid probe that hybridises to the nucleic acid molecule under stringent conditions to form a hybrid double-stranded molecule, the hybrid double-stranded molecule having an unhybridised portion of the nucleic acid probe strand at any portion corresponding to a mutation associated with the susceptibility profile; and detecting the presence or absence of an unhybridised portion of the probe strand as an indication of the presence or absence of a susceptibility-associated mutation.

According to a further aspect of the invention, there is provided a nucleic acid molecule, which:

i) comprises a sequence recited in any one of accession numbers NM_002874; NM_002913; NM_002468; NM_002819; NM_005314; NM_002309; NM_002310; NM_002411; NM_002123; NM_002855; NM_016186; NM_000521; NM_002703; NM_002300; NM_002372; NM_016445; and NM_013352;

ii) is a fragment of a sequence according to i);

iii) comprises the complement of i) or ii);

iv) hybridizes under high stringency conditions a nucleic acid molecule according to i) or ii); for use in the diagnosis or therapy of a proliferative disease such as cancer or a disease or condition which involves a change in cell differentiation or growth rate.

According to a further aspect of the invention, there is provided a protein, which protein:

i) has an amino acid sequence encoded by a nucleic acid sequence recited in any one of accession numbers NM_002874; NM_002913; NM_002468; NM_002819; NM_005314; NM_002309; NM_002310; NM_002411; NM_002123; NM_002855; NM_016186; NM_000521; NM_002703; NM_002300; NM_002372; NM_016445; and NM_013352;

ii) is a fragment of a protein according to i), provided that said fragment retains a biological activity possessed by the full length polypeptide of i) or ii), or has an antigenic determinant in common with the polypeptide of i) or ii);

for use in the diagnosis or therapy of a proliferative disease such as cancer or a disease or condition which involves a change in cell differentiation or growth rate.

The invention also includes ligands, such as antibodies, which bind specifically to, and which preferably inhibit the activity of a protein that comprises an amino acid sequence encoded by a nucleic acid sequence recited in any one of accession numbers NM_002874; NM_002913; NM_002468; NM_002819; NM_005314; NM_002309; NM_002310; NM_002411; NM_002123; NM_002855; NM_016186; NM_000521; NM_002703; NM_002300; NM_002372; NM_016445; and NM_013352. Such ligands may be used in the manufacture of a medicament for the diagnosis or therapy of a proliferative disease such as cancer or a disease or condition which involves a change in cell differentiation or growth rate.

The biological sample used in the methods of the invention is preferably a tissue sample. Any tissue sample may be used, such as blood, urine, saliva, or a specific tissue biopsy. Preferably, cells are isolated using non-invasive procedures, for example, by isolating circulating tumour cells to provide the necessary material for biomarker measurement.

The invention also provides a method of treating a disease in a patient in need of such treatment by administering to a patient a therapeutically effective amount of a protein, a nucleic acid molecule or ligand as described above. Such compounds may be administered in the form of a pharmaceutical composition. Such a composition will include the compound in conjunction with a pharmaceutically-acceptable carrier. Such a compound may be administered in conjunction with an HDAC inhibitor, for example, by separate, simultaneous or sequential administration.

The invention also provides a method of monitoring the therapeutic treatment of a disease or physiological condition in a patient, comprising monitoring over a period of time the level of expression or activity of a protein, nucleic acid molecule, or ligand according to any one of the above-described aspects of the invention in a tissue from said patient, wherein altering said level of expression or activity over the period of time towards a control level is indicative of regression of said disease or physiological condition. The level of expression or activity of a gene or its encoded protein at a first time point may be compared to the expression of the same expression product at a second time point, wherein a change in expression or activity at the second time point relative to the first time point may be correlated with the regression or progression of a disease in which the gene is implicated.

A still further aspect of the invention provides a method of treating a proliferative disease or condition (as described above) which involves a change in cell differentiation or growth rate by modulating the acetylation state of any one of the proteins encoded by hHRAD23B, RFC1, MYD88, PTBP1, PPP4R1, LIF, LIFR, SCBGB2A2, HLA-DQB1, PVRL1, SERPA10, HEXB, PPAT, LDHB, MAN2A1, PLECK2 and SART2. Such a method may modulate the acetylation state of more than one of these proteins, for example, 2, 3, 4, 5, 6, 7, 8 or all 9. Preferably, the acetylation state of these proteins is reduced according to the invention.

The methods described herein may be carried out in vivo or in vitro.

In a further aspect, the invention provides a method for the identification of a compound that is effective in the treatment and/or diagnosis of a proliferative disease such as cancer or a disease or condition which involves a change in cell differentiation or growth rate, comprising contacting a protein, nucleic acid molecule, or ligand according to any one of the above-described aspects of the invention with one or more compounds suspected of possessing binding affinity for said protein, nucleic acid molecule or ligand, and selecting a compound that binds specifically to said nucleic acid molecule, protein or ligand.

According to a still further aspect of the invention, there is provided a kit useful for diagnosing a patient, particularly for assessing suitability for HDAC treatment, comprising a first container containing a nucleic acid probe that hybridises under stringent conditions with a nucleic acid molecule according to any one of the aspects of the invention described above; a second container containing primers useful for amplifying said nucleic acid molecule; and instructions for using the probe and primers for facilitating the diagnosis. The kit may additionally comprise a third container holding an agent for digesting unhybridised RNA.

To facilitate in the diagnosis using one of the methods outlined above, in a further aspect, the invention provides an array of at least two nucleic acid molecules, wherein each of said nucleic acid molecules either corresponds to the sequence of, is complementary to the sequence of, or hybridises specifically to a nucleic acid molecule according to any one of the aspects of the invention described above. Such an array may contain nucleic acid molecules that either correspond to the sequence of, are complementary to the sequence of, or hybridise specifically to at least 1-9 or more of the nucleic acid molecules as recited above. The nucleic acid molecules on the array may consist of oligonucleotides of between twelve and fifty nucleotides, more preferably, between forty and fifty nucleotides. Alternatively, the nucleic acid molecules on the array may consist of PCR-amplified cDNA inserts where the nucleic acid molecule is between 300-2000 nucleotides.

In a related aspect, again useful for diagnosis, the invention provides an array of antibodies, comprising at least two different antibody species, wherein each antibody species is immunospecific with a protein as described above. The invention also provides an array of proteins, comprising at least two protein species as recited above.

Kits useful in the diagnostic methods of the invention may comprise such nucleic acid, antibody and/or protein arrays.

According to the invention, a kit may also comprise one or more antibodies that bind to a protein as recited above, and a reagent useful for the detection of a binding reaction between the antibody and the protein.

According to a still further aspect of the invention, there is provided a genetically-modified non-human animal that has been transformed to express higher, lower or absent levels of a protein according to any one of the aspects of the invention described above. Preferably, said genetically-modified animal is a transgenic or knockout animal. Most preferably, the genetically-modified animal is a rodent, such as a mouse.

The invention also provides a method for screening for a compound effective to treat a disease condition, by contacting a non-human genetically-modified animal as described above with a candidate compound and determining the effect of the compound on the physiological state of the animal.

The practice of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al., Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y.

Unless defined otherwise, all technical and scientific terms used herein have the same meaning as commonly understood by one of ordinary skill in the art to which this invention belongs.

Generally, diseases where susceptibility to HDAC inhibitors may be of interest include cell proliferative disorders such as cancer.

BRIEF DESCRIPTION OF THE FIGURES

FIG. 2 shows genes identified in the knock-down HDAC inhibitor screen. (a) PCR amplification of pRetroSuper inserts from genomic DNA of isolated colonies and BLASTn search of resulting sequence (SEQ ID NOs: 3-24) allowed identification of genes knocked down in SAHA-resistant colonies. These genes were then prioritized according to likelihood of involvement in the cell cycle according to information from literature database searches. (b) Main function, localisation and associated proteins of high probability group of SAHA-sensitivity genes.

FIG. 3 shows the effect of shRNA from pRetroSuper on target genes. Western blot analysis of screen cell extracts from cells expanded from single surviving colonies to determine knockdown off the genes in high priority group identified via the presence of the shRNA insert.

EXAMPLES

Materials and Methods

Cell Culture and Transfection.

Cells were cultured in DMEM (MCF7, U2OS and SAOS2) or RPMI-40 (A2780) containing 10% FCS and 1% penicillin/streptomycin (Gibco). U2OS cells were transfected with synthesised short hairpin siRNAs (Dharmacon) as indicated using oligofectamine (Invitrogen) to a final concentration of 100 nM before harvesting.

FACS Analysis.

Cells were fixed in 50% ethanol/PBS overnight at 4° C. and incubated for 30 min with 1×RNAse A and 20 ng/ml propidium iodide. Samples were run on a FACScan flow cytometer (BD Bioscience) and analysed using CellQuestPro software.

pRetroSuper RNAi Knockdown Screen.

Figure 1A:
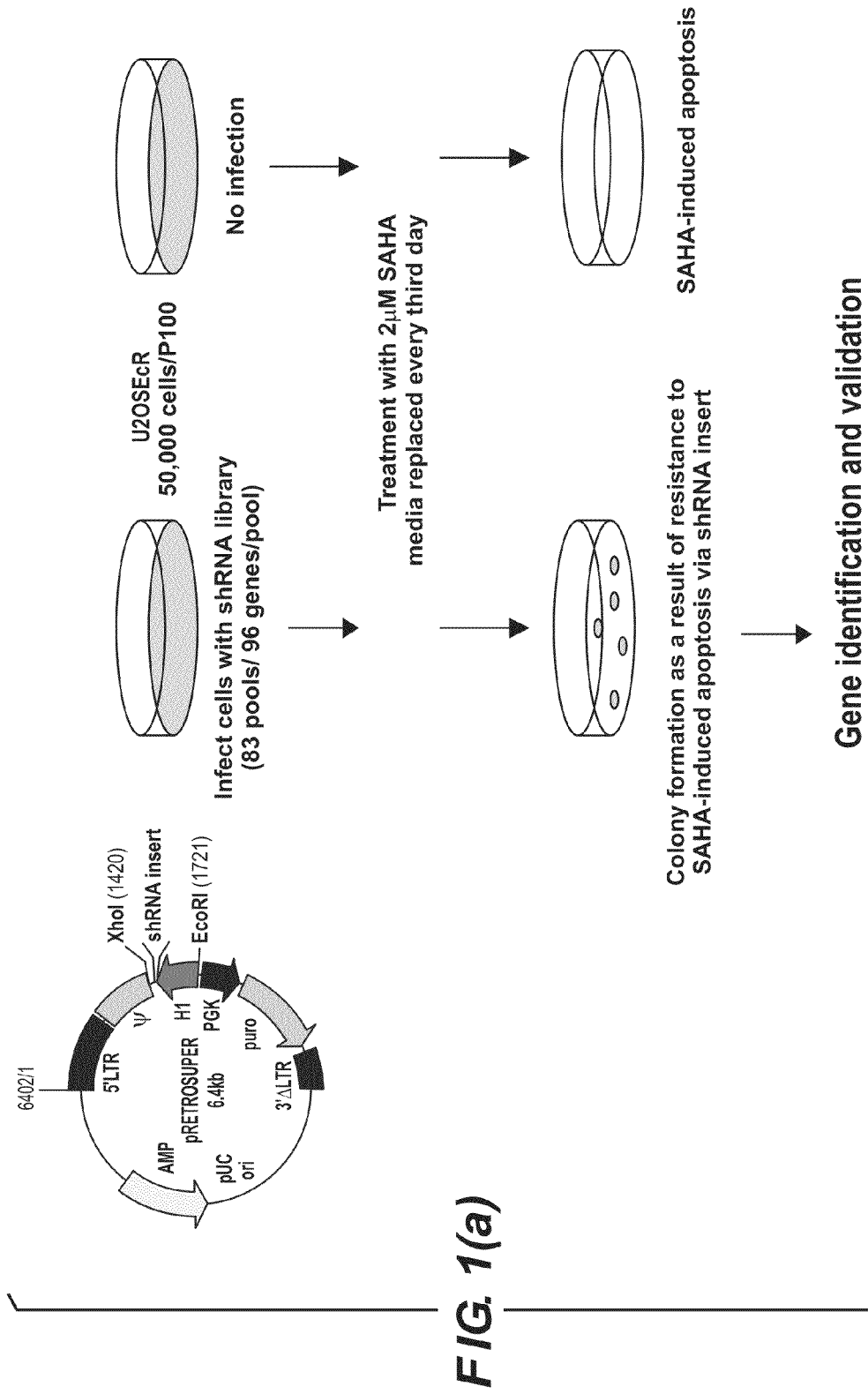
FIG. 1 shows a summary of functional knockdown screen results.
a) Outline of shRNA screening strategy
b) Colonies isolated in the functional screen.

U2OS cells expressing the murine ectropic receptor (U2OSEcR) were infected with the pRetroSuper RNAi library (Brummelkamp et al, 2002a/b). Each pool of the library contained 100 siRNAs per well. Cells were allowed to recover for up to 72 hours to allow for siRNA expression and knockdown and were then plated overnight (40,000 cells per plate). 2 µl SAHA was then added to each plate (cell number and SAHA concentration were determined prior to the screen). SAHA containing media was then replaced every 3 days for 18-30 days until the appearance of colonies on plates co-treated with SAHA and the viral library. Colonies were then picked and expanded to allow isolation of total genomic DNA and total protein (FIG. 1).

DNA Isolation, PCR and Gene Identification.

Genomic DNA was isolated from colony cells using lysis buffer (100 mM Tris pH8.5, 0.2% SDS, 200 mM NaCl and 100 µg/ml proteinase K) and left at 37° C. for 30 minutes with shaking to allow DNA to precipitate. One volume of isopropanol was then added to the lysate and the DNA precipitate dissolved in 10 mM Tris pH7.5, allowing it to be used in PCR to determine the identity of the gene in question. PCR was carried out using the Expand Long Template PCR System (Roche). The genomic insert was recovered by using the primers: pRS forward: 5'-CCCTTGGAACCTCCTCGTTC-GACC-3' (SEQ ID NO:1) and pRS reverse: 5'-CAGACGT-GCTACTTCCATTTGTC-3' (SEQ ID NO:2). Each PCR was analysed on 1.2% 1×TBE/Agarose gel. The PCR product was then sequenced (Lark Technologies) to allow the gene of interest to be identified.

Immunoblotting.

Cells were washed with PBS and lysed in TNN lysis buffer (50 mM Tris pH 8, 120 mM NaCl, 0.5% NP-40, 1 mM dithiothreitol, and protease inhibitors) at 4° C. for 20 min. The extracts were centrifuged at 16,000 g for 10 min to remove cell debris. Cell lysate was normalised (Bradford assay) and equal protein loading was confirmed with Ponceau S staining. Total protein was resolved by denaturing SDS-polyacrylamide gel electrophoresis (PAGE) before electrotransfer to Protran nitrocellulose membrane, and subsequently probed with antibody. The antibodies used were RFC-1, MYD88, LIF, LIFR and hnRNPI (Santa Cruz Biotechnology), and hHR23B (Biomol). Enhanced chemi-luminescence (Pierce) was used to visualize antibody binding.

1. A Functional Knock-Down Screen for Drug Sensitivity Genes.

The shRNA knock-down screen (Brummelkamp et al, 2002a) involves the use of an shRNA (in pRetroSuper) library targeting greater than 8,000 human genes and contains three shRNA expressing vectors for each gene. The siRNAs produced from the shRNAs induce a strong and specific suppression of gene expression (Brummelkamp et al., 2002a, b) and the stable expression of siRNAs using pRetroSuper mediates suppression of gene expression over prolonged periods of time. This allows the analysis of loss-of-function phenotypes in long term assays.

We refined the screen to enable the identification of genes necessary for HDAC-inhibitor induced apoptosis to be identified. The rationale behind the screen is that the knock-down of genes required for HDAC inhibitor induced apoptosis would allow cells to proliferate and grow in the presence of the HDAC inhibitor (FIG. 1). These cells can then be isolated, the identity of the knock-down genes determined and, thereafter, the role of the genes validated in functional assays. From 132 colonies, about 25 produced DNA sequence that enabled the identity of the target genes to be determined (this may result from cells becoming infected with more than one virus shRNA construct). The genes targeted by the siRNA (FIG. 2a) were arbitrarily divided into three groups based on the likelihood that they were involved in pathways involved with proliferation control; the key features of the genes are summarised in FIG. 2b.

To confirm that the gene identified via the shRNA DNA sequence was in fact knocked-down, the expression level of certain of the encoded proteins was investigated. Almost complete knock-down was observed in the case of the LIF receptor and RFC1, whilst partial knockdown was observed in the case of MYD88, hnRNP I and hHR23B (for LIF, the quality of the antibody was very poor, and an antibody was not available to PP4R1, so these two genes could not be finally validated). RT-PCR was also carried out using gene specific primers to determine the RNA levels of these genes in cells containing the pRetroSuper insert (FIG. 3a).

Figures 4A, 4B:
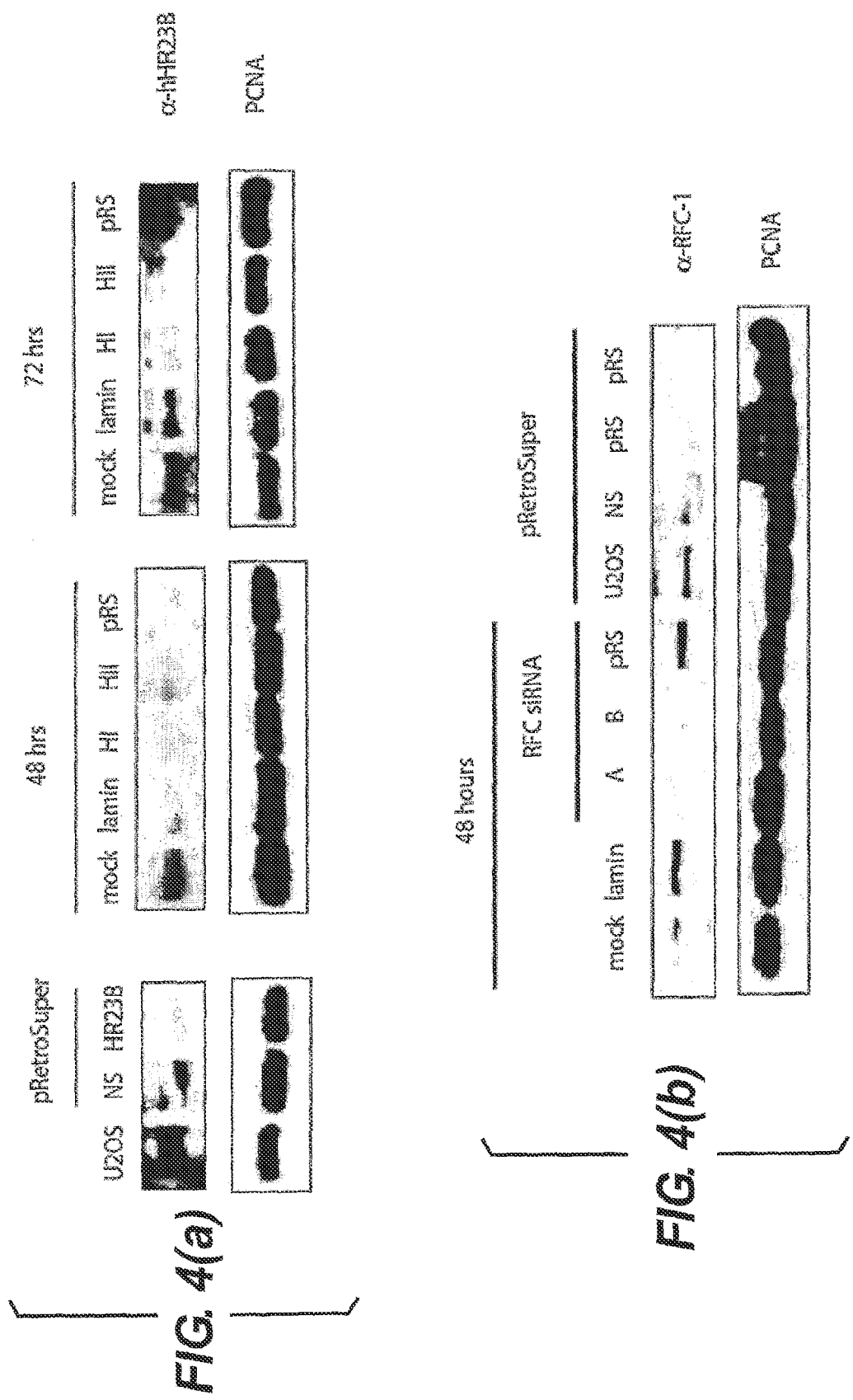
FIG. 4 shows a comparison of stable versus transient knockdown. (a) Two knockdown vectors against hHR23B (HI and HII) along with a short hairpin siRNA containing the pRetroSuper insert sequence were transiently transfected into U2OS cells for 48 or 72 hours to determine if similar levels of knockdown could be produced compared to control siRNA. (b) Two knockdown vectors were produced against RFC-1 (A and B) along with a short hairpin siRNA containing the pRetroSuper insert sequence were transiently transfected into U2OS cells for 48 hours. Levels of both genes were then compared to the levels of knockdown observed in the cells isolated from the screen. PCNA was used as a loading control. NS=non-specific pRetroSuper, pRS=pRetroSuper.

The sequence within the pRetroSuper vector was compared to that of synthetic siRNAs targeting the same sequence as the pRetroSuper insert. Two other synthetic siRNAs derived from other regions of the RNA and previously shown to cause knockdown of RFC-1 and hHR23B were also investigated (Anderson and Perkins, 2003; Glockzin et al, 2003). For hHR23B the siRNA sequence taken from the pRetroSuper vector produced efficient knock-down when introduced as an siRNA after 48 hours, whilst two other synthetic unrelated sequences targeting hHR23B RNA (HI and HII) also produced efficient knockdown (FIG. 4). The level of knockdown produced by the hHR23B shRNA after 48 hours treatment was comparable to that of the stable knock-down cells. Knock-down of RFC-1 by the two other sequences (RA and RB) was very efficient after 48 hours whereas the synthetic siRNA against the sequence from the pRetroSuper insert did not cause knockdown after 48 hours treatment (FIG. 4). The level of knock-down by the shRNAs A and B was comparable to that of the stable cell lines from the screen. The discrepancies between the level of knock-down could be a result of the different mechanisms, as an siRNA may be more or less effective depending on the method of delivery (for example transient versus stable expression).

Figure 5A:
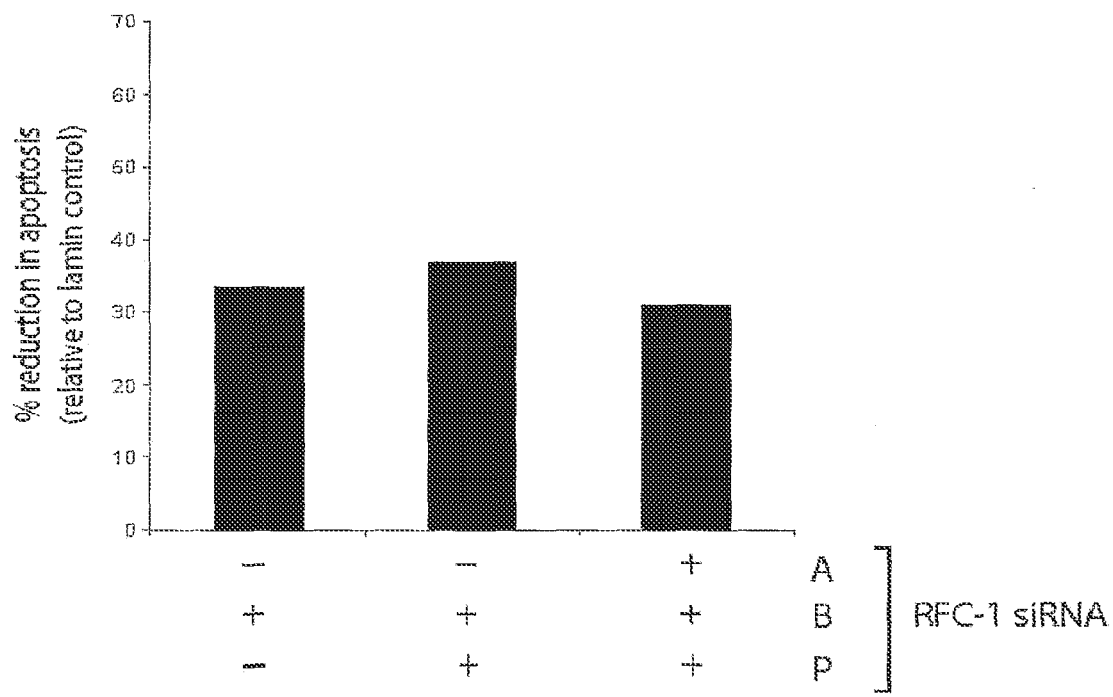
FIG. 5 shows the effect of synthetic siRNA RFC1 on HDAC inhibitor sensitivity. a) U2OS cells were treated with siRNA RFC1 followed by SAHA (as described) and the level of sub-G1 (apoptotic) cells measured. The data represent the percentage change in the sub-G1 fraction, in which the control treatment siRNA lamin was set to 100%. b) U2OS cells treated as indicated were immuno-blotted with anti-RFC1 or antilamin A/C.
Figure 5B:
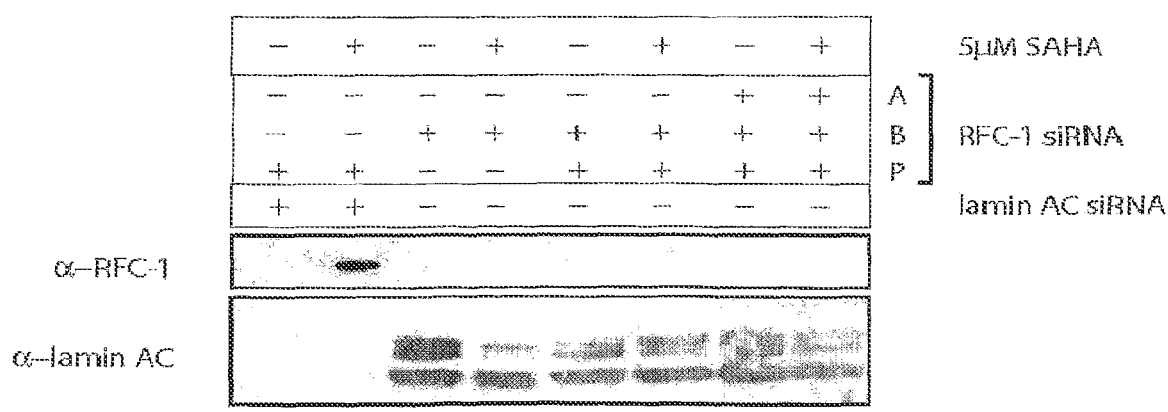

In order to validate the role of the genes identified through the screen in regulating sensitivity to HDAC inhibition, we assessed the effect of knock-down on HDAC inhibition. Considering Rad23B and RFC1, the introduction of siRNAs against distinct regions of each gene reduced the sensitivity of U2OS cells to HDAC inhibitor-induced apoptosis (FIG. 5). For siRNA RFC1, the reduction in the level of apoptosis was very significant, reaching as high as 35%. The effect of siRNA RFC1 thus validates the approach as a platform to identify genes that influence sensitivity to HDAC inhibitors.

Importantly, the platform can now be applied to other types of drugs, particularly where the cessation of cellular proliferation is the outcome of the drug treatment. The pathways involved in HDAC inhibitor mediated apoptosis are most likely to be quite diverse but through the functional siRNA knock-down screen described here it has been possible to identify the critical regulatory pathways affected by HDAC inhibitors and necessary for the apoptotic outcome.

It is possible that the proteins identified through the knock-down screen are themselves modified by acetylation, or alternatively interact with other proteins subject to acetylation control, allowing them to be modified and function in pathways required for apoptosis. Elucidating the role of these novel effector proteins may identify essential pathways which are targeted by HDAC inhibitors and necessary for the induction of apoptosis. Equally, these genes could encode biomarkers which allow tumours to be stratified into groupings that are likely to undergo more favourable responses to HDAC inhibitors. Most importantly, the screening strategy described here is generally applicable in that it can be applied to cancer drugs against other targets.

REFERENCES

Anderson L A and Perkins N D. (2003) Regulation of RelA (p65) function by the large subunit of replication factor C. Mol. Cell. Biol. 23 (2) 721-732.

Bedalov A, Gatbonton T, Irvine W P, Gotschling D E, and Simon J A. (2001) Identification of a small moleculae inhibitor of Sir2p. Proc. Natl. Acad. Sci. USA. 98, 15113-15118.

Brummelkamp, T. R., Bernards, R., and Agami, R. (2002a). Stable suppression of tumorigenicity by virus-mediated RNA interference. Cancer Cell 2, 243-247.

Brummelkamp, T. R., Bernards, R., and Agami, R. (2002b). A system for stable expression of short interfering RNAs in mammalian cells. Science 296, 550-553.

Butler L M, Zhou X, Xu W-S, Scher H I, Rifkind R A, Marks P A and Richon V M. (2002). The histone deacetylase inhibitor SAHA arrests cancer cells growth, upregulates thioredoxin-binding protein-2 and down-regulates thioredoxin. Proceedings of the National Academy of Sciences of the USA 99, (18) 11700-5.

Della Ragione F, Criniti V, Della Pietra V, Borriello A, Oliva A, Indaco S, Yamamoto T, Zappia V. (2001) Genes modulated by histone acetylation as new effectors of butyrate activity. FEBS Letters 499, (3) 199-204

Dyson, N. (1998). The regulation of E2F by pRb-family proteins. Genes Dev. 12, 2245-2262.

Glaser K B, Stayer M J, Waring J F, Stender J, Ulrich R G and Davidson Sk (2003). Gene expression profiling of multiple histone deacetylase (HDAC inhibitors: defining a common gene set produced by HDAC inhibition in T24 and MDA carcinoma cell lines. Mol. Cancer Ther. 2, 151-163.

Glockzin S, Ogi F-X, Hengstermann A, Scheffer M and Blattner C (2003). Involvement of the DNA repair protein hHR23 in p53 degradation. Mol. Cell. Biol. 23 (24) 8960-969.

Grozinger C M, Chao E D, Blackwell H E, Moazed D and Schreiber S L. (2001). Identification of a class of small molecular inhibitors of the sirtuin family of NAD-dependent deacetylases by phenotypic screening. J. Biol. Chem 276 (42) 38837-38843

Inche, A. and La Thangue, N. B. (2006) Chromatin control and cancer drug discovery: realising the promise. Drug Discovery Today (in press).

Jacobson, S. & Pilius, L. (1999). Modifying chromatin and concepts of cancer. Curr. Op. Genet. Dev. 9, 175-184.

Johnstone, R. W. (2002). Histone deacetylase inhibitors: novel drugs for treatment of cancer. Nat. Rev. Drug. Disc. 1, 287-299.

Johnstone R W. (2002) Histone-deacetylase inhibitors: novel drugs for the treatment of cancer. Nat Rev Drug Discov. 4, 287-99.

Liang P and Pardee A B (2003). Analysing differential gene expression in cancer. Nat. Rev. Cancer 3, 869-876.

McLaughlin, F. & LaThangue, N. B. (2002). Tumour classification for tailored cancer therapy. Ann. Rep. in Med. Chem. 37, (Ch 23) 225-233.

McLaughlin, F. and La Thangue, N. B. (2003). Histone deacetylase inhibitors in psoriasis therapy. Inflammation and Allergy. 3, 213-219.

Marks P A, Richon V M, Breslow R, Rifkind R A. (2001) Histone deacetylase inhibitors as new cancer drugs. Curr Opin Oncol. 6 477-83.

Mitsiades C S Mitsiades N S, McMullan C J, Poulaki V, Shringarpue R, Hideshima T, Akiyama M, Chauhn D, Munshi N, Gu X, Bailey C, Joseph M, Libermann T A, Richon V M, Marks P A and Anderson K C. (2004). Transcriptional signature of histone deacetylase inhibition in multiple myeloma: biological and clinical applications. Proc. Natl. Acad. Sci. USA. 101 (2) 540-545.

Suzuki H, Gabrielson E, Chen W, Anbazhagan R, van Engelend M, Weijenberg M P, Herman J G abd Baylin S. (2002). A genomewide screen for genes upregulated by demethylation and histone deacetylase inhibiton in human colorectal cancer. Nat Genetics 31 (2) 141-149.

Van Lint C, Emiliani S, Verdin E. (1996) The expression of a small fraction of cellular genes is changed in response to histone hyperacetylation. Gene Expression. 5 (4-5) 245-53.

Vaziri, H., Dessain, S. K., Ng Eaton, E., Imai, S-I., Frye, R. A., Pandita, T. K., Guarente, L. & Weinberg, R. (2001). hSIR2 (SIRT1) Functions as an NAD-dependent p53 deacetylase. Cell 107, 149-159.

The invention claimed is:

1. A method of diagnosing the susceptibility of an individual suffering from cancer to treatment with an HDAC inhibitor, the method comprising assessing the level of expression or activity of a gene's expression product in a sample from a patient and comparing said level of expression or activity to a reference, wherein a level of expression or activity that is different to said reference is indicative of an altered susceptibility to treatment with the HDAC inhibitor relative to the reference state, wherein said gene is hHRAD23B (human rad 23B), wherein the expression product is a protein, and wherein the protein is detected by an antibody that binds specifically to the hHRAD23B protein, and wherein the sample comprises tumor cells.

2. The method of claim 1, wherein a level that is significantly higher than the reference level indicates that the individual is more susceptible to treatment with an HDAC inhibitor, and wherein if a significantly higher level is detected then the method further comprises referring the patient for treatment with the HDAC inhibitor.

3. The method of claim 1, wherein the method further comprises treating said patient with an HDAC inhibitor if they are found to be susceptible to treatment with an HDAC inhibitor.

4. The method of claim 1, wherein a level that is significantly lower than the reference level is indicative of an individual's potential resistance to treatment with the HDAC inhibitor.

5. The method of claim 1, wherein the hHRAD23B gene is a nucleic acid molecule, which:
   (a) comprises a hHRAD23B sequence recited in accession number NM_002874.3 (SEQ ID NO:25); or
   (b) is a fragment of a sequence according to (a).

6. The method of claim 1, wherein the expression product is a protein, which:
   (a) has an amino acid sequence encoded by a nucleic acid sequence of claim 5(a); or
   (b) is a fragment of a protein according to (a), provided that said fragment retains a biological activity possessed by the full length polypeptide of (a) of modulating the transfer of proteins from the site of ubiquitination to the proteasome, or has an antigenic determinant in common with the polypeptide of (a).

7. The method of claim 1, wherein the method of diagnosis is facilitated by an array comprising at least two different types of antibody species, wherein each antibody species is immunospecific with a hHRAD23B protein.

8. The method of claim 1, wherein said sample is a tissue sample.

9. The method of claim 8, wherein said sample is blood, urine, saliva, or a specific tissue biopsy.

10. A kit for diagnosing the susceptibility of an individual suffering from a disease to treatment with an HDAC inhibitor comprising:
   (a) one or more antibodies that binds to hHRAD23B; and
   (b) a reagent useful for the detection of a binding reaction between the antibody and the protein.

11. A method of treating a patient with a proliferative disease such as cancer or a disease or condition which involves a change in cell differentiation or growth rate, wherein said treatment comprises administering an HDAC inhibitor, and wherein said patient has been identified as susceptible to HDAC inhibitor treatment using the method of claim 1.

12. The method of claim 11, wherein said treating comprises administering hHRAD23B protein or nucleic acid molecule in conjunction with the HDAC inhibitor by separate, simultaneous or sequential administration.

13. The method of claim 11, wherein the method additionally comprises monitoring the therapeutic treatment of the disease or physiological condition in a patient, comprising monitoring over a period of time the level of expression or activity of a HR23B protein or nucleic acid molecule, in a sample from said patient, wherein altering said level of expression or activity over the period of time towards a control level is indicative of regression of said disease or physiological condition.

14. A method of diagnosing the susceptibility of an individual suffering from a disease to treatment with an HDAC inhibitor, the method comprising assessing the level of expression of a gene or the sequence of a gene in a sample from a patient and comparing said level of expression or sequence to a reference, wherein a level of expression or sequence that is different to said reference is indicative of an altered susceptibility to treatment with the HDAC inhibitor relative to the reference state, and wherein said gene is hHRAD23B (human rad 23B), wherein the method comprises the steps of:
   (a) isolating a nucleic acid molecule encoding hHRAD23B from a sample from a patient being tested for disease; and
   (b) diagnosing the patient by detecting the presence of a mutation which is associated with an altered susceptibility to treatment with the HDAC inhibitor,
   or wherein the method comprises the steps of:
   (i) contacting a sample of tissue from the patient with a nucleic acid probe under stringent conditions that allow the formation of a hybrid complex between a nucleic acid molecule coding for hHRAD23B and the probe;
   (ii) contacting a reference sample with the probe under the same conditions used in step (i); and
   (iii) detecting the presence of hybrid complexes in said samples.

15. A method of diagnosing the susceptibility of an individual suffering from cancer to treatment with an HDAC inhibitor, the method comprising assessing the level of expression or activity of a gene or its expression products, or the sequence of a gene, in a sample from a patient and comparing said level of expression or activity or sequence to a reference, wherein a level of expression or activity or sequence that is different to said reference is indicative of an altered susceptibility to treatment with the HDAC inhibitor relative to the reference state, wherein said gene is hHRAD23B (human rad 23B), and wherein the disease is cancer, and wherein the sample comprises tumor cells.

16. A method of diagnosing the susceptibility of an individual suffering from cancer to treatment with an HDAC inhibitor, the method comprising assessing the level of expression or activity of a gene or its expression products, or the sequence of a gene, in a sample from a patient and comparing said level of expression or activity or sequence to a reference, wherein a level of expression or activity or sequence that is different to said reference is indicative of an altered susceptibility to treatment with the HDAC inhibitor relative to the reference state, and wherein said gene is hHRAD23B (human rad 23B), wherein a level that is significantly higher than the reference level indicates that the individual is more susceptible to treatment with an HDAC inhibitor, and wherein if a significantly higher level is detected then the method further comprises treating said patient with an HDAC inhibitor, and wherein the sample comprises tumor cells.

17. The method of claim 14, wherein the method of diagnosis is facilitated by an array comprising at least two nucleic acid molecules, wherein each of said nucleic acid molecules corresponds to the sequence of, is complementary to the sequence of, or hybridises specifically to a hHRAD23B nucleic acid molecule.

* * * * *

SEQUENCE LISTING

<160> NUMBER OF SEQ ID NOS: 25

<210> SEQ ID NO 1
<211> LENGTH: 24
<212> TYPE: DNA
<213> ORGANISM: Artificial Sequence
<220> FEATURE:
<223> OTHER INFORMATION: synthetic primer

<400> SEQUENCE: 1
cccttggaac ctcctcgttc gacc                                              24

<210> SEQ ID NO 2
<211> LENGTH: 23
<212> TYPE: DNA
<213> ORGANISM: Artificial Sequence
<220> FEATURE:
<223> OTHER INFORMATION: synthetic primer

<400> SEQUENCE: 2
cagacgtgct acttccattt gtc                                               23

<210> SEQ ID NO 3
<211> LENGTH: 19
<212> TYPE: DNA
<213> ORGANISM: Homo sapiens

<400> SEQUENCE: 3
gatgcaacga gtgcacttg                                                    19

<210> SEQ ID NO 4
<211> LENGTH: 19
<212> TYPE: DNA
<213> ORGANISM: Homo sapiens

<400> SEQUENCE: 4
cagattaagg gtgctatga                                                    19

<210> SEQ ID NO 5
<211> LENGTH: 19
<212> TYPE: DNA
<213> ORGANISM: Homo sapiens

<400> SEQUENCE: 5
acacaacttc agtcgatag                                                    19

<210> SEQ ID NO 6
<211> LENGTH: 18
<212> TYPE: DNA
<213> ORGANISM: Homo sapiens

<400> SEQUENCE: 6
ggaccgttta tcatgagc                                                     18

<210> SEQ ID NO 7
<211> LENGTH: 19
<212> TYPE: DNA
<213> ORGANISM: Homo sapiens

<400> SEQUENCE: 7
acacagcttt ccacagggc                                                    19

<210> SEQ ID NO 8
<211> LENGTH: 19

```
<212> TYPE: DNA
<213> ORGANISM: Homo sapiens

<400> SEQUENCE: 8
caacctggac aagctatgt                                              19

<210> SEQ ID NO 9
<211> LENGTH: 19
<212> TYPE: DNA
<213> ORGANISM: Homo sapiens

<400> SEQUENCE: 9
caggccgtgg tactgatta                                              19

<210> SEQ ID NO 10
<211> LENGTH: 19
<212> TYPE: DNA
<213> ORGANISM: Homo sapiens

<400> SEQUENCE: 10
taatcagtac cacggcctg                                              19

<210> SEQ ID NO 11
<211> LENGTH: 19
<212> TYPE: DNA
<213> ORGANISM: Homo sapiens

<400> SEQUENCE: 11
ttaatatatg acagcagtc                                              19

<210> SEQ ID NO 12
<211> LENGTH: 19
<212> TYPE: DNA
<213> ORGANISM: Homo sapiens

<400> SEQUENCE: 12
ttaatatatg acagcagtc                                              19

<210> SEQ ID NO 13
<211> LENGTH: 19
<212> TYPE: DNA
<213> ORGANISM: Homo sapiens

<400> SEQUENCE: 13
gagatcgtgc gcttcgaca                                              19

<210> SEQ ID NO 14
<211> LENGTH: 18
<212> TYPE: DNA
<213> ORGANISM: Homo sapiens
<220> FEATURE:
<221> NAME/KEY: misc_feature
<222> LOCATION: 10
<223> OTHER INFORMATION: n = A,T,C, G, unknown or other

<400> SEQUENCE: 14
gtgcagtatn agcctgag                                               18

<210> SEQ ID NO 15
<211> LENGTH: 19
<212> TYPE: DNA
<213> ORGANISM: Homo sapiens

<400> SEQUENCE: 15
```
agatctccat gaggcacga                                                      19

<210> SEQ ID NO 16
<211> LENGTH: 19
<212> TYPE: DNA
<213> ORGANISM: Homo sapiens

<400> SEQUENCE: 16
acatgagaca aagaatagc                                                      19

<210> SEQ ID NO 17
<211> LENGTH: 19
<212> TYPE: DNA
<213> ORGANISM: Homo sapiens

<400> SEQUENCE: 17
atcacgtctt tactgaaga                                                      19

<210> SEQ ID NO 18
<211> LENGTH: 19
<212> TYPE: DNA
<213> ORGANISM: Homo sapiens

<400> SEQUENCE: 18
ggatatacca actgggcta                                                      19

<210> SEQ ID NO 19
<211> LENGTH: 19
<212> TYPE: DNA
<213> ORGANISM: Homo sapiens

<400> SEQUENCE: 19
gttaagccgc cagttcacc                                                      19

<210> SEQ ID NO 20
<211> LENGTH: 19
<212> TYPE: DNA
<213> ORGANISM: Homo sapiens

<400> SEQUENCE: 20
gttaagccgc cagttcacc                                                      19

<210> SEQ ID NO 21
<211> LENGTH: 19
<212> TYPE: DNA
<213> ORGANISM: Homo sapiens

<400> SEQUENCE: 21
gaaattagcc tgagcactg                                                      19

<210> SEQ ID NO 22
<211> LENGTH: 19
<212> TYPE: DNA
<213> ORGANISM: Homo sapiens

<400> SEQUENCE: 22
gaaattagcc tgagcactg                                                      19

<210> SEQ ID NO 23
<211> LENGTH: 19
<212> TYPE: DNA
<213> ORGANISM: Homo sapiens

<400> SEQUENCE: 23

```
gaaattagcc tgagcactg                                              19
```

```
<210> SEQ ID NO 24
<211> LENGTH: 19
<212> TYPE: DNA
<213> ORGANISM: Homo sapiens
<220> FEATURE:
<221> NAME/KEY: misc_feature
<222> LOCATION: 6
<223> OTHER INFORMATION: n = A,T,C, G, unknown or other

<400> SEQUENCE: 24
ttaacnggac aaactatgt                                              19
```

```
<210> SEQ ID NO 25
<211> LENGTH: 4130
<212> TYPE: DNA
<213> ORGANISM: Homo sapiens
<220> FEATURE:
<223> OTHER INFORMATION: RAD23 homolog B, GenBank Accession NM_002874.3

<400> SEQUENCE: 25
gggggcacgt ctcggcgagt cacgatgatg gcggccacca tcctgtggtg agctagcgga    60
ttccctgctt gtctcgccga cccctcgcg ccttctgcag actccgtggc tggcgctcgg   120
cgcgtgagga agcacggcgg cccgagttcg cggggaaggc cgcagtcgcg gaggcagcgg   180
cgcggtccgg ggcacgggct gggggagagg ccgctccgct gggcgaatgt gacaagcccc   240
cacccccacc gccttcctcc ccagagcgcg aggagcgcgg gcgaccccgg ggccccgcca   300
ggccacagac cccgcccagc ggccagcacc cggcgcaggc ccggcagccg agctgcgcgg   360
cggcaccatg caggtcaccc tgaagaccct ccagcagcag accttcaaga tagacattga   420
ccccgaggag acggtgaaag cactgaaaga gaagattgaa tctgaaaagg ggaaagatgc   480
ctttccagta gcaggtcaaa aattaattta tgcaggcaaa atcctcaatg atgatactgc   540
tctcaaagaa tataaaattg atgagaaaaa ctttgtggtg gttatggtga ccaaacccaa   600
agcagtgtcc acaccagcac cagctacaac tcagcagtca gctcctgcca gcactacagc   660
agttacttcc tccaccacca caactgtggc tcaggctcca acccctgtcc ctgccttggc   720
ccccactccc acacctgcat ccatcactcc agcatcagcg acagcatctt ctgaacctgc   780
acctgctagt gcagctaaac aagagaagcc tgcagaaaag ccagcagaga caccagtggc   840
tactagccca acagcaactg acagtacatc gggtgattct tctcggtcaa ccttttttga   900
agatgcaacg agtgcacttg tgacgggtca gtcttacgag aatatggtaa ctgagatcat   960
gtcaatgggc tatgaacgag agcaagtaat tgcagccctg agagccagtt tcaacaaccc  1020
tgacagagca gtggagtatc ttttaatggg aatcccttgga gatagagaaa gtcaggctgt  1080
ggttgacccc cctcaagcag ctagtactgg ggctcctcag tcttcagcag tggctgcagc  1140
tgcagcaact acgacagcaa caactacaac aacaagttct ggaggacatc cccttgaatt  1200
tttacggaat cagcctcagt ttcaacagat gagacaaatt attcagcaga tccttcctt  1260
gcttccagcg ttactacagc agataggtcg agagaatcct caattacttc agcaaattag  1320
ccaacaccag gagcatttta ttcagatgtt aaatgaacca gttcaagaag ctggtggtca  1380
aggaggagga ggtggaggtg gcagtggagg aattgcagaa gctggaagtg gtcatatgaa  1440
ctacattcaa gtaacaccte aggaaaaaga agctatagaa aggttaaagg cattaggatt  1500
tcctgaagga cttgtgatac aagcgtattt tgcttgtgag aagaatgaga atttggctgc  1560
```

-continued

```
caatttcctt ctacagcaga actttgatga agattgaaag ggactttttt atatctcaca    1620
cttcacacca gtgcattaca ctaacttgtt cactggattg tctgggatga cttgggctca    1680
tatccacaat acttggtata aggtagtaga ttgttggggg tggggaggga gggatctagg    1740
atacagggca gggataaata cagtgcatgt ctgcttcaat tagcagatgc cgcaactcca    1800
cacagtgtgt aaaatatata caaccaaaaa tcagcttttg caggtcttta tttcttctgt    1860
aaaacagtag gtaacttttc ctaggtttca ctcttttag tgtactagat ccagaaactt     1920
agtgtaatgc cctgctttat atttctttga cttaacattg gtttcagaaa gaatcttagc    1980
tacctagaat ttacagtctc tgtttcatgg caacactgga taatggcttt gtgaaattta    2040 aaaaatttt gtagcgactg taaacagaaa tgccaaattg atggttaatt gttgctgctt     2100
caaaaataag tataaaatta atatgtaagg aagcccattc tttcatgtta aatacttggg    2160
gtgggagggg agaaagggaa ccttttctta aaatgaaaat aattactgct attttaaaat    2220
ttcttgatca ttgaatgtga gacccttcta acatgatttg agaagctgta caagtatagg    2280
cagagttatt ttcctgttta cattttttt ttgttttggg gaaaaaattg gtaggtgtct     2340
aattactgtt tacttcattg ttatattgca gtaaaagttt taaaacaacc attgcatgtt    2400
tgcttttgat gtatcccttt gtgaaattag cacttttggg gccaatggag aaatgcagca    2460
ttcactctcc ctgtcttttc cccttccctc agcagaaacg tgtttatcag caagtcgtga    2520
gtcaaactgc tgccttttaa aaaacccaca aaatgctgat tcagttcaaa attaatgcaa    2580
atgtttcaaa actgggtttc tgatatttgt aaatgtgttt ctttattaga taagagtgta    2640
ttaccattaa agtcattagt ataatattgc tttcaaaaag aaatggtaga caaaactata    2700
atccagcatc ttttattgca ttggaaagac tggcaaagtc ttttggatgg gttgggagat    2760
gtggctggaa agtactttgg aaaatataca atcaagatat ctcatggcat attaaaagaa    2820
aaatcttaat agcagtgttg gcttttattt ggatttttc atctcagttt tttctgtgga    2880
atctccttca ttggcattgt tatttaatca taaacggggc agatgtctac ttgttcagtt    2940
tttcaaatct gttttcctga gtataaataa gagtatttaa agaaataatt tggattgctt    3000
ttgttttttg tttcctttt tttaaccatc tgatactaag aagatgaatt tgcacagatt     3060
tctctgcata atttctcaat atcttttagca cagtatggtg atgatgactt ttaagcattt    3120
acatcacgta ctcataacct attatgaaaa taaatgaaac tggctgggta tggtggctca    3180
tgcctataat cccagcactt tgggaggccg aggtgggcag atcacttgag gccaggagat    3240
tgagaccagc ctgaccgtca tggcgaaacc ccgtctctac taaaaataca aaaaatagcc    3300
aggcatggtg gcgcacgcct gtggtcccag ctacttggga ggctgaggca tgagaattgc    3360
ttgaacccgg gaagtgaagg ttgccgtgag ctgagatcac accactgcca taaacatgac    3420
aggcttttgg actttgtatt acctgtatgt tttataatgg atcatgcata atttctcagg    3480
agaataaaat gagaattcat atatacgttc atctttcaag tcagagcaat gagttgggaa    3540
aagaggtggc atttctgatc ggataatgga atactctcat ttattttatg acattctctg    3600
tctactcaga tcatagtgaa aactggaaac aaaaaaaaaa aacagcctct tcttggaaag    3660
tgacagcaga aggtggcatg gagcttgtgt ccttggacaa caaatctgga tatactagga    3720
ttaattatca gaagacagct caggccaagt tttgatcgtt ccatacagta ccttgtttat    3780
```

```
ctgcttctta aagaatcagc cgagacacca taaaagaaat aggcttttg tgccttttgc    3840 tgttaatgtt taatttacaa actgttttgg taaatctctt aatgtaagta gctatttgac   3900
tttggaattt tgcattcgag gtatactgtc atttcttgaa atctttttct cgtttagttg   3960
ctctgtggga aatgtgagga agcctaagtt tgtatttgta aatttcttat gccatcctct   4020
agtcaaattt tttttcattg tttaaaaata cggaagtgtt ccaatataat tttttcctgt   4080
actggatggc taggattcta gagaattgat tataaaatat tttcaataca              4130
```